US00PP14818P3

(12) United States Plant Patent
Danziger

(10) Patent No.: US PP14,818 P3
(45) Date of Patent: May 25, 2004

(54) GYPSOPHILA PLANT NAMED 'DANFESTAR'

(50) Latin Name: *Gypsophila paniculata*
Varietal Denomination: Danfestar

(75) Inventor: Gabriel Danziger, Nir-Zvi (IL)

(73) Assignee: Danziger "DAN" Flower Farm (IL)

( * ) Notice: Subject to any disclaimer, the term of this patent is extended or adjusted under 35 U.S.C. 154(b) by 9 days.

(21) Appl. No.: 10/277,155

(22) Filed: Oct. 22, 2002

(65) Prior Publication Data

US 2004/0078858 P1 Apr. 22, 2004

(51) Int. Cl.[7] ..... A01H 5/00

(52) U.S. Cl. ..... Plt./354

(58) Field of Search ..... Plt./354

*Primary Examiner*—Kent Bell
(74) *Attorney, Agent, or Firm*—Foley & Lardner

(57) ABSTRACT

A new and distinct Gypsophila plant named 'Danfestar' characterized by being suitable for gardening outdoors, in containers and as a small sized cut flower; forms a flowering bush with a 10–15 inch spread in 2–3 months; compact dense branched plant with plenty of flowering stems; medium, semi-filled white flowers, early flowering, having a long lasting flowering flush; and perennial plant that will come back after winter.

2 Drawing Sheets

Latin name of the genus and species of the plant claimed: *Gypsophila paniculata.*

Variety denomination: 'Danfestar'; commercial denomination: Gypsophila cv. Festival Star.

BACKGROUND OF THE INVENTION

The present invention relates to a new and distinct cultivar of Gypsophila plant, botanically known as *Gypsophila paniculata*, hereinafter referred to by the cultivar name 'Danfestar'.

The new cultivar was derived from an open pollination with a proprietary female cultivar and unknown male parent made in a controlled breeding program in Moshav Mishmar Hashiva, Israel. The female parent is hybrid no. 589 (unpatented, proprietary cultivar). The male parent is an open pollination. 'Danfestar' was discovered and selected by the inventor, Gabriel Danziger, as a flowering plant within the progeny of the open pollination in a controlled environment in Moshav Mishmar Hashiva, Israel.

Asexual reproduction of the new cultivar by side shoot cuttings was first performed in 1999 in Moshav Mishmar Hashiva, Israel and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Danfestar' which in combination distinguish this Gypsophila as a new and distinct cultivar:

1. Suitable for gardening outdoors, in containers and as a small sized cut flower;
2. forms a flowering bush of 10–15 inch spread in 2–3 months;

3. compact dense branched plant with plenty of flowering stems;
4. medium, semi-filled white flowers, early flowering, having a long lasting flowering flush; and
5. perennial plant that will come back after winter.

'Danfestar' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Moshav Mishmar Hashiva, Israel under conditions which closely approximate those generally used in commercial practice.

Of the many commercial cultivars known to the present inventor, the most similar in comparison to 'Danfestar' is the cultivar Gypsophila cv. 'Happy Festival' (U.S. Plant Pat. No. 9,711 under variety denomination 'Danghappy'). In comparison to 'Danfestar', 'Happy Festival' has a more compact growth habit and dense inflorescence; smaller flowers than those of 'Danfestar' and is better suited as a 4 inch pot plant.

The following is a comparison between 'Danfestar' and the female parent.

TABLE 1

| Characteristic | 'Danfestar' | Female parent 589 |
|---|---|---|
| Plant height | 40–50 cm | 80–90 cm |
| Commerical product | Pot and bedding plant | Cut flower |

BRIEF DESCRIPTION OF THE DRAWING

The accompanying photographic drawings show a typical specimen plant of 'Danfestar', with colors as true as possible with illustrations of this type. The first photographic drawing shows a flowering 'Danfestar' bush in a 12 inch container (3 months from planting). The second photographic drawing shows a flowering 'Danfestar' bush in a garden, labeled '1774', its original designation during testing (2 months from planting).

DETAILED BOTANICAL DESCRIPTION

The following observations, measurements and values describe the new cultivar as grown in Moshav Mishmar Hashiva, Israel under conditions which closely approximate those generally used in commercial practice. Color references are made to The Royal Horticultural Society Colour Chart (R.H.S.), except where general colors of ordinary significance are used. Color values were taken under daylight conditions at approximately 12:00 pm in Moshav Mishmar Hashiva, Israel. The plants described are 8 weeks from planting.

Optimal growing conditions of plant: For outdoor gardening, plant in full sunlight starting early spring. The plant can overcome moderate winter growing outside. For spring sales, plant at weeks 6–8 in a greenhouse in a 4 inch pot. Use artificial light to extend day time up to 16 houres during winter to stimulate flowering. Use light well drained soil. Irrigate and fertilize moderately.

General observations: 'Danfestar' is a heavily branched, round symmetrical bush, reaching a height of 30–50 cm; a large number of upright secondary stems (10–15 depending on growing conditions); develop and flower within a short time and stay in bloom for more than a month, for each flowering cycle; white, semi-full flowers, depending on growing conditions, 5–6 mm in flower diameter, arranged densely in bunches at stem tips; no changes in color or distortions of the flower were noted. Flowering stems can be picked for domestic use having a long vase life. For outdoor gardening plant in full sunlight starting in early spring. This variety flowers within 6–7 weeks from planting in summer and 9–10 weeks during fall. Plants can overcome winter outside, flowering in early spring of the second year. Fully grown plants keep flowering even through moderate winter. Prune moderately at the end of the flowering flush, to renew growth and flowering.

Propagation: Stem Cutting.

Plant:

*General appearance and form.*—Height: 30–50 cm. Width: 30–40 cm. Habit: Bush. Form: Bush symmetrical, round and densely branched. Flowering Response: During long day conditions. Flowering Season: Summer, spring and fall. In winter with light supplement. Winter Hardiness: Half hardy plant can withstand temperature down to 0° C. Lastingness of the Individual Bloom: 10–14 days. Rooting: Apply rooting hormone, keep wet, avoid direct sunlight. Fragrance: Typical of Gypsophila.

Foliage:

*Overall shape of leaf.*—Lanceolate.

*Attachment.*—Sessile.

*Base.*—Truncate.

*Apex.*—Acuminate.

*Margin.*—Entire.

*Texture.*—Rough.

*Main color of upper surface.*—Mature leaf: Green 137-C. Immature leaf: Green 137-D.

*Main color of lower surface.*—Mature leaf: Green 137-C. Immature leaf: Green 137-D.

*Venation color.*—None.

*Leaf size.*—Length: 4–5 cm. Width: 6–7 mm.

*Stipules.*—None.

Inflorescence:

*Natural flowering season.*—Long day.

*Corolla.*—Form/shape: Rounded cup. Average Number: Approximately one thousand per flowering stem. Size: 5–6 mm in diameter. Petal Number: 40–50 (In long day conditions with high light intensity). Petal Shape: Spathulate with emarginate tip. Petal Markings: None. Petal Color: Upper surface: White 155-D. Lower surface: White 155-D. Sepals: Shape: Lanceolate. Length: 3 mm. Width: 1 mm. Apex: Acuminate. Margin: Entire. Color: Green, RHS 144A.

*Stem.*—Average length: 40–50 cm. Average diameter: 2 mm. Color: Yellow-Green 144-B. Internode length: 2.5–3 cm.

*Spur.*—None.

*Bud.*—Response: Long day. Color: White 155-D. Size before opening: Width 3 mm, length 4 mm. Shape: Oroid. Pedicel Length: 8–9 mm. Pedicel Color: Yellow-Green 144-B.

Reproductive organs observed:

*Pistil.*—2, white RHS 155D. Pollen: Scarce.

*Stigma.*—2, Convex, white 155-D.

*Ovary.*—Color yellow-green 144-D.

*Fruit/seed.*—None.

Disease resistance: No observations to date.

I claim:

1. A new and distinct Gypsophila plant named 'Danfestar', substantially as illustrated and described herein.

* * * * *

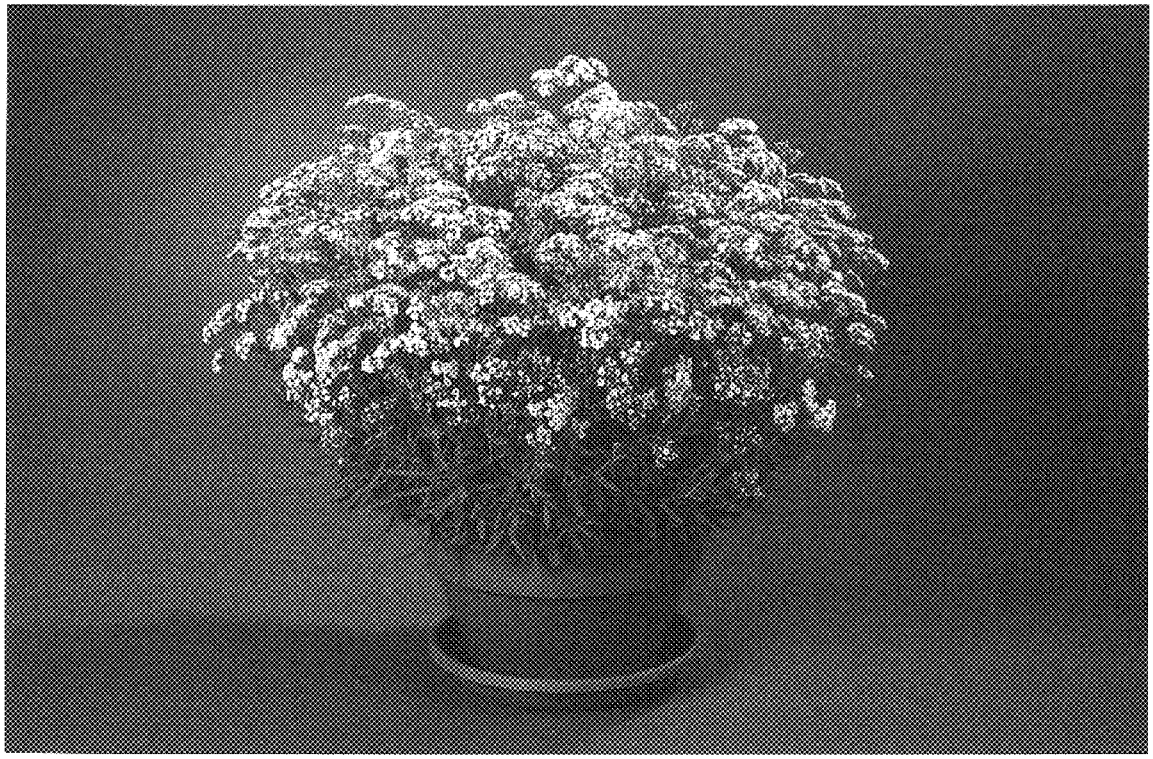

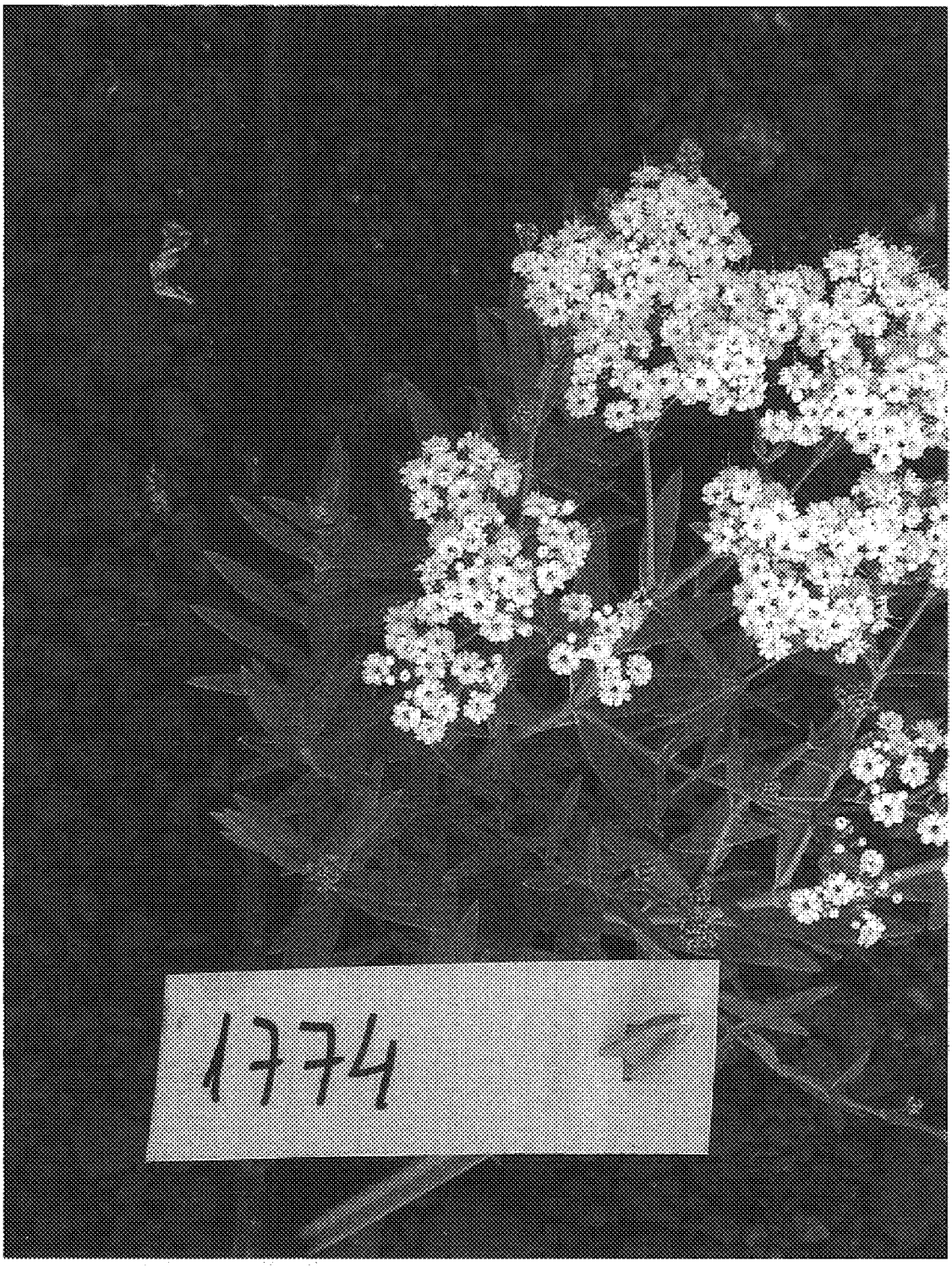
1774